United States Patent [19]

Blake, III

[11] Patent Number: 4,789,090
[45] Date of Patent: Dec. 6, 1988

[54] SURGICAL STAPLER

[76] Inventor: Joseph W. Blake, III, 88 Main St., New Canaan, Conn. 06840

[21] Appl. No.: 926,631

[22] Filed: Nov. 3, 1986

[51] Int. Cl.⁴ .............................................. A61B 17/04
[52] U.S. Cl. ................ 227/19; 227/DIG. 1; 227/155
[58] Field of Search ............... 227/19, DIG. 1, 143, 227/144, 155

[56] References Cited

U.S. PATENT DOCUMENTS

| | | | |
|---|---|---|---|
| 1,674,437 | 6/1928 | Hubbard | 227/132 |
| 1,744,700 | 1/1930 | Hubbard et al. | 227/132 |
| 2,231,539 | 2/1941 | Larsen | 227/120 |
| 2,240,455 | 4/1941 | Carlile | 227/88 X |
| 3,638,847 | 2/1972 | Noiles et al. | 227/DIG. 1 |
| 3,873,016 | 3/1975 | Fishbein | 227/83 |
| 4,043,504 | 8/1977 | Hueil et al. | 227/19 X |
| 4,127,227 | 11/1978 | Green | 227/19 X |
| 4,166,466 | 9/1979 | Jarvik | 227/19 X |
| 4,179,057 | 12/1979 | Becht et al. | 227/19 |
| 4,180,196 | 12/1979 | Hueil et al. | 227/109 |
| 4,185,762 | 1/1980 | Forehlich | 227/19 X |
| 4,196,836 | 4/1980 | Becht | 227/DIG. 1 |
| 4,202,480 | 5/1980 | Annett | 227/DIG. 1 |
| 4,204,623 | 5/1980 | Green | 227/DIG. 1 |
| 4,257,725 | 3/1981 | Foslier | 227/19 |
| 4,406,392 | 9/1983 | Campbell et al. | 227/19 |
| 4,410,125 | 10/1983 | Noiles et al. | 227/19 |
| 4,427,008 | 1/1984 | Transue | 227/19 X |
| 4,448,194 | 5/1984 | DiGiovanni | 227/DIG. 1 |
| 4,519,532 | 5/1985 | Foslien | 227/DIG. 1 |
| 4,523,707 | 6/1985 | Blake, III et al. | 227/DIG. 1 |
| 4,618,086 | 10/1986 | Li et al. | 227/DIG. 1 |

FOREIGN PATENT DOCUMENTS

711115 10/1941 Fed. Rep. of Germany .
00968 4/1982 PCT Int'l Appl. .

Primary Examiner—Paul A. Bell
Attorney, Agent, or Firm—Lackenbach Siegel Marzulo & Aronson

[57] ABSTRACT

A surgical stapler for suturing tissue that includes a flat driver slidably mounted in a stapler frame in operative association with a substantially flat anvil rotatably mounted in the frame. The anvil includes a projection, or flange, that is located near the nose of the stapler frame. The driver has a staple-forming recess at the nose area. The anvil is rotated by activation of the driver via a trigger mounted in the frame means. When the anvil is rotated from a non-engaged position to an engaged position by action of the driver, the projection of the anvil drops on the inner side of a staple in the recess. Further outward movement of the driver crimps the staple in the recess between the projection and the driver. De-engagement of the driver from the staple results in forcing the anvil to rotate from the engaged position to the non-engaged position so as to free the crimped staple from its position in the recess.

36 Claims, 8 Drawing Sheets

SURGICAL STAPLER

This invention relates to surgical stapling instruments and more particularly to a skin stapler that is disposable after a single use.

In recent years, surgical skin staples have been used as sutures to close incisions and wounds of the skin or fascia of a patient rather than conventional thread sutures. The stapling instruments, or surgical staplers, that have been developed to apply the surgical staples vary widely and no one type of surgical stapler has been widely accepted by doctors. The defects of these prior art staplers are too various to be listed here, but it can be said that one of the most common defects is the possibility of sending an extra staple to the stapling station at the crimping recess at the nose of the stapler with certain problems thereupon occurring. The primary problem is that of two staples occurring in the crimping recess. From this malfunction, one of the following events could occur: (1) the surgical stapler may jam during the operation; (2) the surgical stapler may be rendered inoperative during the operation; (3) a distorted or partially formed staple may be applied the wound.

Often the cause of double staples is that the user may stop part way through the stapling cycle. The possible causes of a stop are too numerous to mention here, but some examples of stoppages are a change of mind, distraction, accident, mistake, movement by the patient, and lack of knowledge of exactly how the stapler functions. Another problem encountered in surgical staplers is that a closed staple embedded in the skin of the patient must be decoupled by a mechanism in the stapler or by certain specific manual movements so that tearing of the skin does not occur.

A prior art skin stapler device that has provided a mechanism against double loading of staples in the stapler is disclosed in U.S. Pat. No. 4,523,707 issued June 18, 1985 to Blake and Kaufman.

It is, therefore, a principal object of this invention to provide a unique and novel medical stapler for suturing the skin or fascia.

It is another object of the present invention to provide a surgical stapler that disallows any return to the original position of the stapling cycle if the use stops after the stapling cycle has been initiated by the user.

It is yet another object of the present invention to provide a surgical stapler that prevents two or more staples being positioned at the staple crimping recess to the stapler.

It is yet another object of the present invention to provide a surgical stapler of the disposable type that automatically and positively decouples the closed staple from the stapler at the completion of the stapling cycle.

It is a further object of the present invention to provide a surgical stapler that automatically decouples the closed staple from the stapler at the completion of the stapling cycle.

Additional objects of the present invention are low cost of manufacture, ease of assembly, and fewer parts.

SUMMARY OF THE INVENTION

In accordance with the above objects and others which will become apparent, there is herein set forth a surgical stapler for suturing tissue by at least one staple comprising a stapler frame adapted to be held by hand and having a nose, the frame being adapted to hold the staple and to direct the staple at the tissue site, the frame further having a hand grip. An elongated, substantially flat anvil pivotably mounted in the frame has an anvil face portion at the nose, the anvil face portion being movable between non-engaged and engaged positions. An elongated, substantially flat driver is slidably, or movably, mounted in the frame in operative relationship with the anvil. The driver has a crimping recess including an outer positioning pocket and an inner crimping pocket proximate the nose of the frame. The staple is capable of being shaped from an open staple to a crimped staple. The driver is adapted to form the crimped staple in association with the anvil in the crimping recess. The driver is movable between activated and inactivated positions, wherein in the activated position the driver has forced the anvil face portion from the nonengaged position to the engaged position; and wherein in the de-activated position the driver has forced the anvil face portion from the engaged position to the non-engaged position and is simultaneously decoupled from the crimped staple relative to the crimping recess. A manually operated trigger is movably mounted to the frame and is adapted to move the driver from the de-activated position to the activated position. A return spring connected to the frame and to the trigger is adapted to move the driver from the activated position to the de-activated position. The anvil is pivotably mounted to the frame. The anvil face portion is flanged toward the driver at the outer end of the anvil, so that in the engaged position, the anvil flange is positioned in front of the staple so that when the driver is activated the open staple is crimped in the inner crimping pocket between the anvil and the driver. In the non-engaged position the anvil flange is rotated away from the crimping recess. At least one camming mechanism mounted with the anvil and driver is adapted to force the anvil to rotate between the engaged and non-engaged positions.

BRIEF DESCRIPTION OF THE DRAWINGS

The present invention will be further described with reference to the accompanying drawings.

DESCRIPTION OF THE PREFERRED EMBODIMENTS

Reference is now made to the drawings wherein like reference numerals refer to like parts in the various figures.

Figures 1, 2:
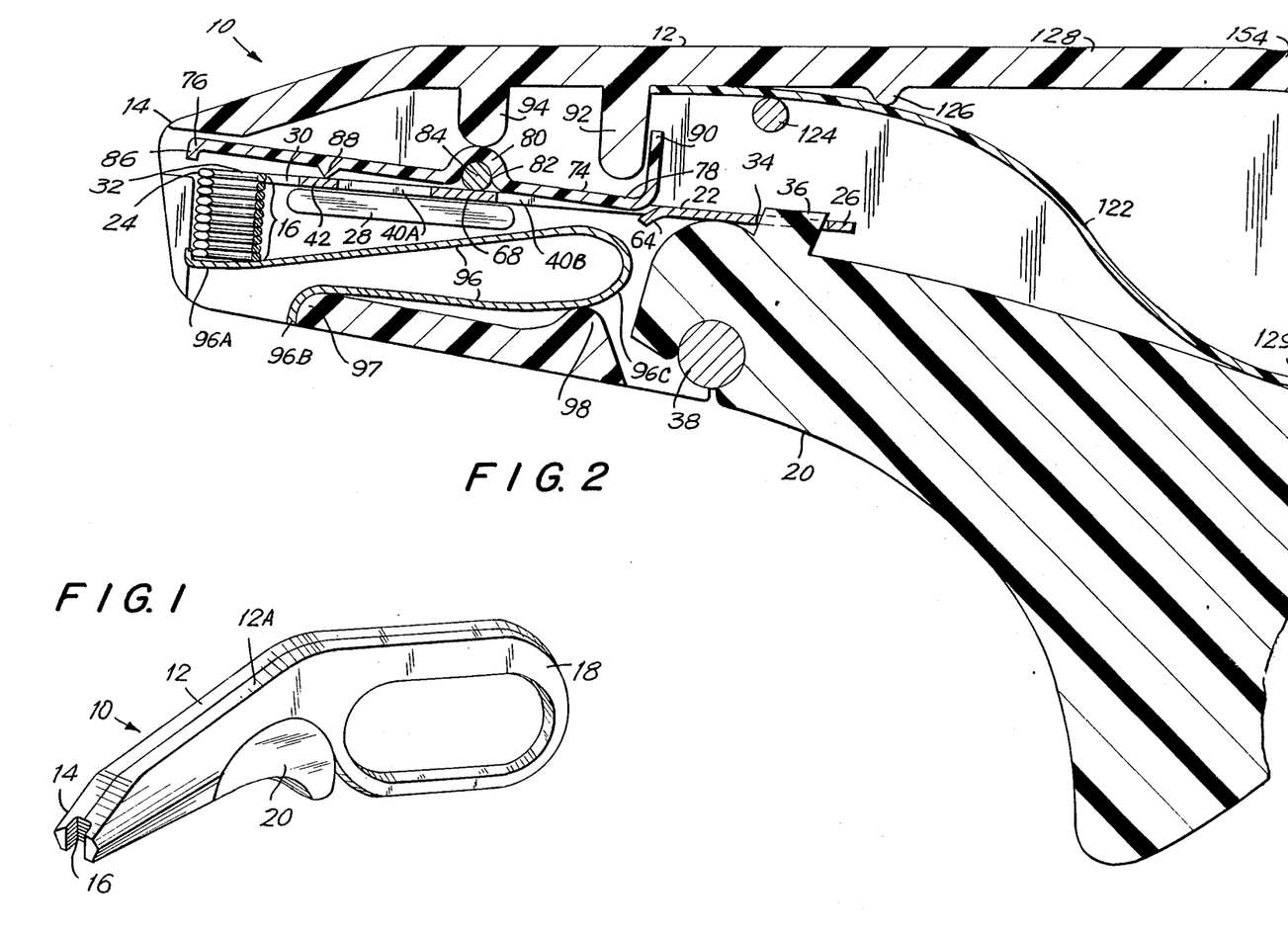
FIG. 1 is a perspective view of the surgical stapler.
FIG. 2 is a partial side sectional view of the surgical stapler in the inactivated position.
Figures 3, 20:
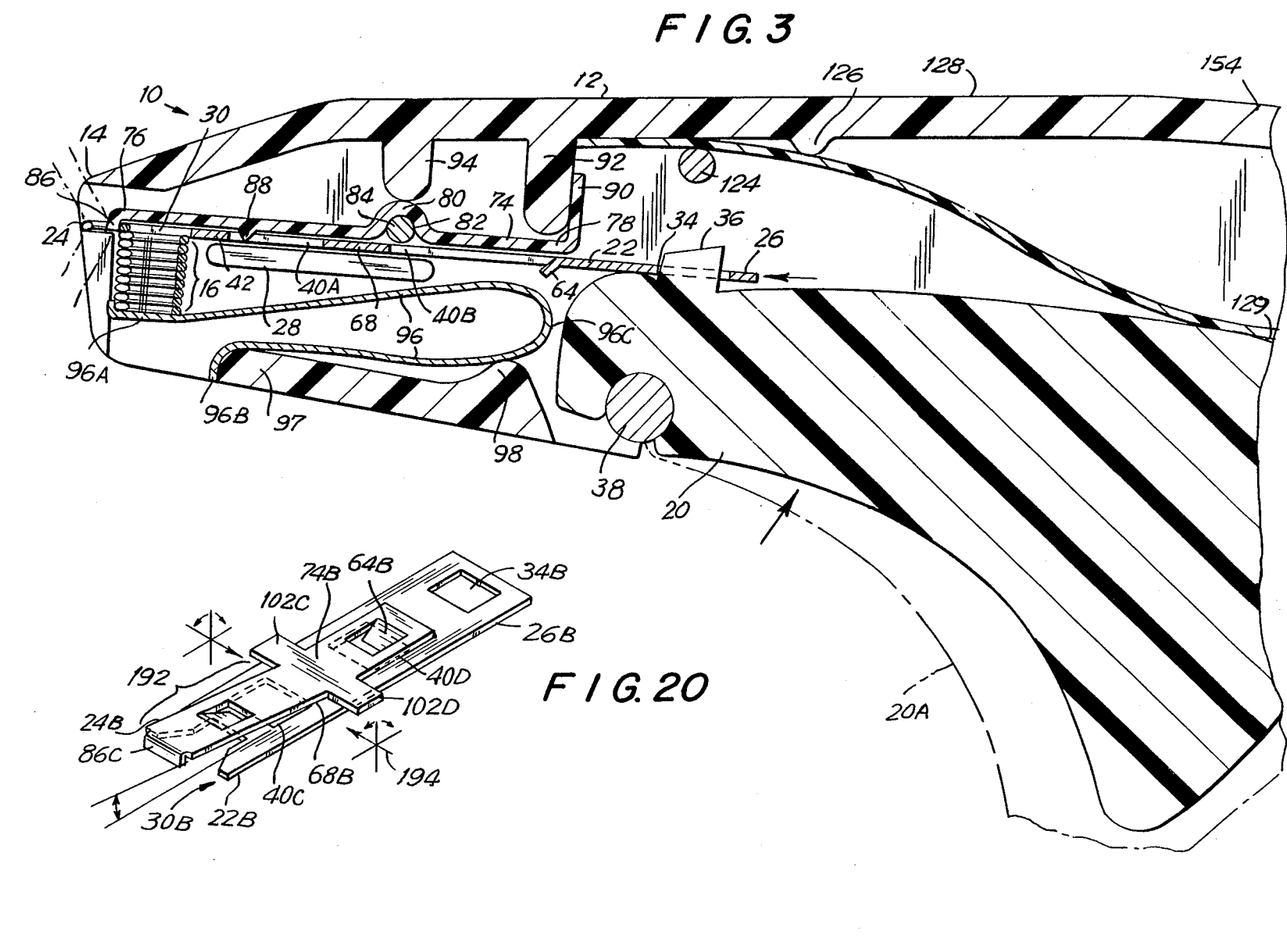
FIG. 3 is a partial sectional view of the surgical stapler in activated position.
FIG. 20 is a perspective view of another embodiment of the stapler mechanism.

FIG. 1 illustrates in perspective view a surgical stapler 10 that includes a frame 12 having a forwardly located thin nose 14 for directing one of a stack of staples 16 at the tissue site, a rearwardly located hand grip 18, and a trigger element 20 adjacent to the hand grip. Stack of staples 16 can alternatively be a cartridge. Stack of staples 16 is preferably approximately 15 staples. The shape of grip 18 and trigger 20 are such as to be conveniently held by hand. FIG. 2 shows a sectioned front portion of stapler 10 in an inactivated mode with trigger 20 at rest in the downward position. FIG. 3 shows stapler 10 with trigger 20 pulled back into an activated mode from the inactivated mode shown as 20A in phantom line. A pusher, or driver, 22 mounted in frame 12 between nose 14 and trigger 20 is an elongated, generally flat member having opposed outer and inner end portions 24 and 26, respectively, with outer end portion 24 being disposed proximate nose 14 and an inner end portion 26 being disposed proximate the top portion of trigger 20. Driver 22 rides upon a flat support element 28 in turn connected to the side walls of frame 12. Driver 22 forms a crimping recess 30 at outer end portion 24 that opens to nose 14. A single open staple 32 is shown positioned adjacent recess 30. Staple 32 is in the plane of driver 22 and stack 16 is below the plane of driver 22. Although stack 16 is shown oriented vertically and the terms "above" and "below" are occasionally used herein for convenience, it is to be understood that stapler 10 can be aligned in any direction. Inner end portion 26 is in operational relationship with the top portion of trigger 20. Specifically, driver 22 has a slot 34 at inner end portion 26 that is adapted to receive a driver finger 36 extending upwardly from the top of trigger 20. The forward side of finger 36 is in contact with the forward edge of slot 34. As seen in FIG. 3, when trigger 20 is activated by the surgeon, finger 36 pushes against driver 22 at slot 34 so as to transitionally move driver 22 within frame 12 along the top of support element 28 to the activated position shown in FIG. 3 Trigger 20 is rotatably connected to pivot 38, which extends transversely within frame 12 and is supported at the side walls of the frame. Driver 22 has a first outward hole 40A spaced inwardly from crimping recess 30 and a second inward hole 40B spaced inwardly from first hole 40A and extending rearwardly to a position spaced forwardly of slot 34. Recess 30 and hole 40A are separated by a transverse camming bar 42.

Figure 4:
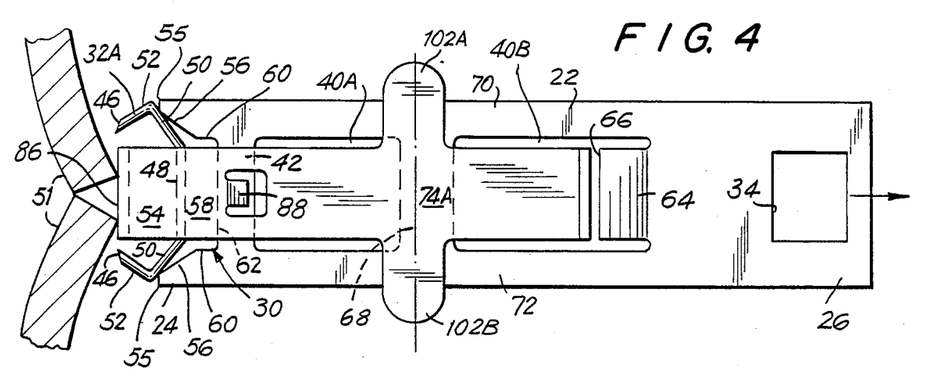
FIG. 4 is a top view of a surgical stapler mechanism in the inactivated position.
Figure 5:
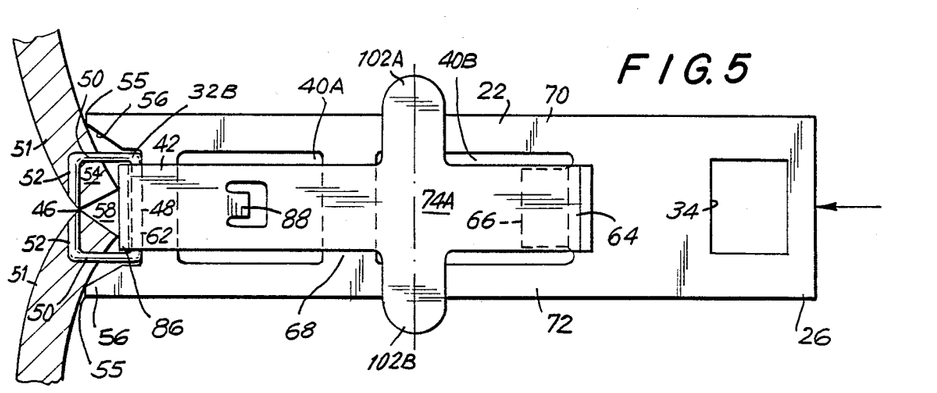
FIG. 5 is a top view of the surgical stapler mechanism like the stapler mechanism shown in FIG. 4 in the activated position.
Figure 6:
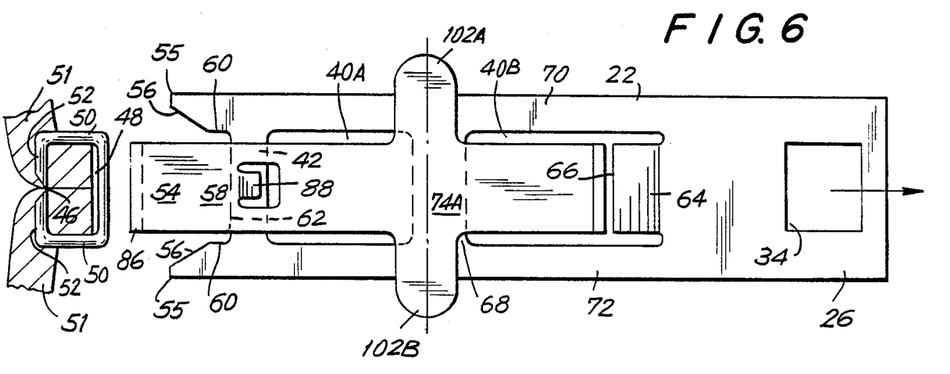
FIG. 6 is a top view of the surgical stapler mechanism like stapler mechanism shown in FIGS. 4 and 5 in the ret position.
Figures 7, 8, 9:
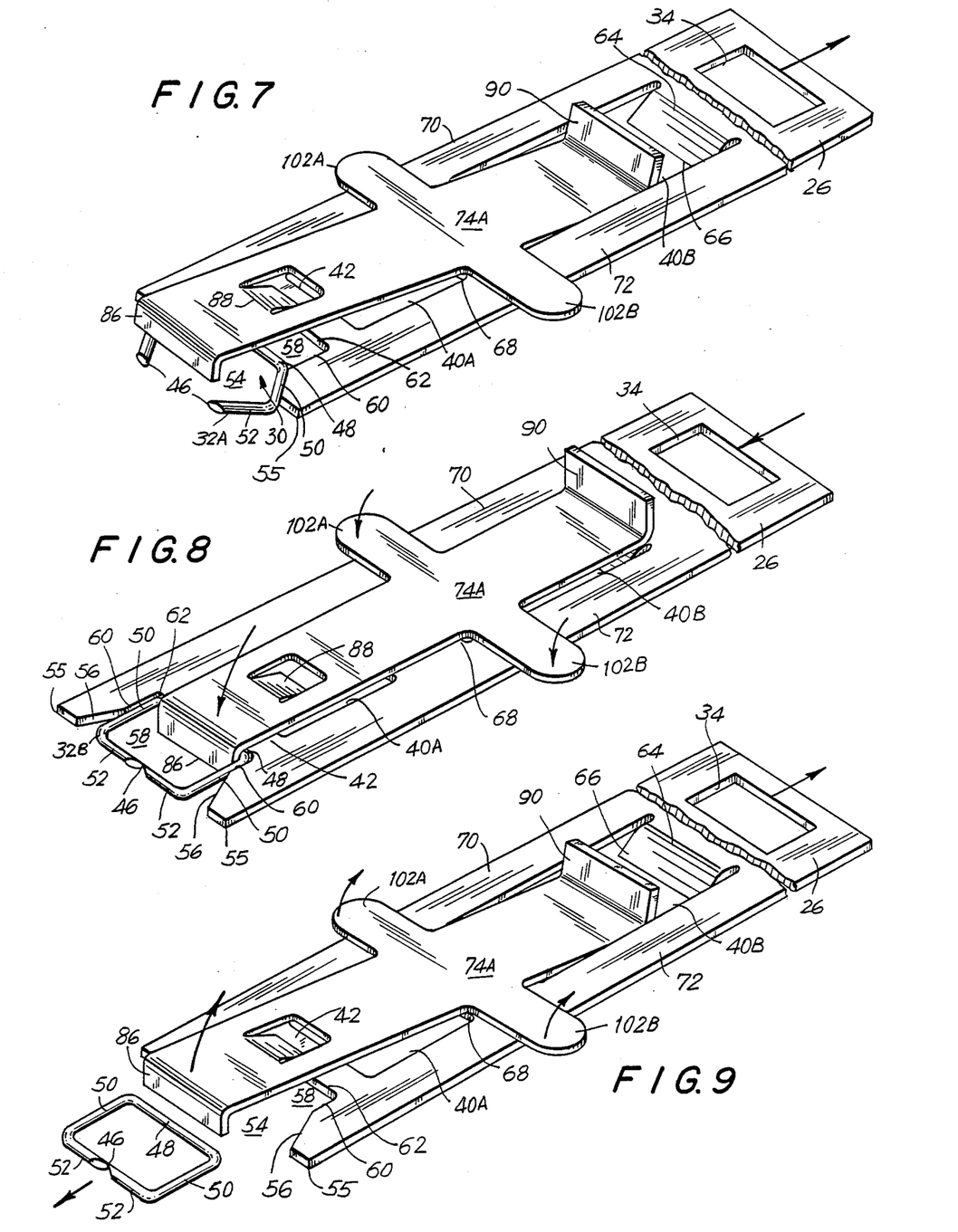
FIG. 7 is a perspective view of the surgical stapler mechanism shown in FIGS. 5-7 in the inactivated position.
FIG. 8 is a perspective view of the surgical stapler mechanism shown in FIG. 7 in the activated position.
FIG. 9 is a perspective view of the surgical stapler mechanism shown in FIGS. 7 and 8 in the inactivated position.

Staple 32, seen best in the simplified embodiments of the invention seen in FIGS. 4–6 and 7–9, has a pair of pointed ends 46, a transverse mid-portion 48, a pair of opposed side portions 50 joined to mid-portion 48, and a pair of opposed cross-portions 52 joined to pointed ends 46 and side portions 50. In the open mode 32A of staple 32 as seen in FIGS. 4 and 7, wherein staple 32 is positioned to suture tissue 51 of the patient shown in FIG. 4, pointed ends 46 are spaced apart and side portions 50 are disposed at an obtuse angle relative mid-portion 48. In the closed mode 32B of staple 32 as seen in FIGS. 5 and 8, wherein staple 32 has sutured tissue 51 of the patient as shown in FIG. 5, pointed ends 46 are in close proximity, crossportions 52 are transverse and parallel to mid-portion 48, and formerly angled side portions 50 are laterally disposed relative frame 12 and are generally perpendicular to transverse mid-portion 48.

As shown in FIGS. 4 and 7, crimping recess 30 includes a first staple positioning pocket 54 disposed at the extreme end of outer end portion 24 adapted to accept staple 32 in its open mode 32A. Opposed angled edges 56 of first pocket 54 are angled slightly away from angled side portions 50 so that only outer, or end, portions 55 of angled edges 56 are in contact with angled side portions 50. As shown in FIGS. 5 and 8, crimping recess 30 also includes a second staple crimping pocket 58 spaced inwardly from first pocket 54 adapted to form staple 32 into its crimped, or closed, mode 32B so that lateral edges 60 of second pocket 58 are in pressing contact with now parallel side portions 50 and rear edge 62 is in pressing contact with mid-portion 48. It is to be particularly noted that during the formation of staple 32 from open mode 32A to closed mode 32B end portions 55 are adapted to press side portions 50 towards one another in the first stages of the crimping of staple 32.

Driver 22 includes a camming ramp 64 spaced from inner end portion 26 and from slot 34; ramp 64 extends downwardly, that is towards the planes of stack of staples 16, from the rear of hole 40B so that a transverse lip 66 at the end of ramp 64 is positioned past the plane of flat driver 22.

In the embodiment shown in FIGS. 1–9, a transverse support bar 68 extends between holes 40A and 40B for connection to opposed, parallel, outer side bars 70 and 72 seen clearly in FIGS. 4–9.

As seen in FIGS. 2–9, an anvil 74 mounted in frame 12 is configured as an elongated flat member having opposed outer and inner end areas 76 and 78, respectively. Anvil 74 lies generally along and over driver 22 and is pivotable relative to driver 22. In the embodiment of FIGS. 2 and 3, anvil 74 forms an upwardly extending transverse shoulder 80 which forms a transverse, semi-cylindrical recess 82 in which a transverse pivot pin 84 is seated. Pivot pin 84 is connected to the side wall of frame 12 in a suitable manner. Anvil 74 is rotatably movable about pivot pin 84.

Anvil 74 includes a transverse flanged anvil face 86 extending across outer end area 76 downwardly in front of mid-portion 48 of staple 32. Anvil face 86 is parallel to and spaced from mid-portion 48 of staple 32 in a non-engaged relationship therewith in the inactivated mode of driver 22 and of stapler 10 generally as shown in FIG. 2. In the activated mode of driver 22 shown in FIG. 3, anvil face 86 is in an engaged position. Anvil 74 also includes a transverse camming ramp 88 located between anvil face 86 and pivot 84. Camming ramp 88 extends downwardly from the bottom side of anvil 74 towards transverse camming bar 42 angled inwardly and rearwardly relative to outer end area 76. Camming ramp 88 is in contact with camming bar 42 of driver 22 when driver 22 is in its non-activated position and anvil 74 is in its non-engaged position. Camming ramp 88 is positioned in the forward part of elongated hole 40A rearward of camming bar when anvil face 86 is in its engaged position. In the activated position, inner end area 78 is cammed up camming ramp 64 to lock anvil 74 in place when crimping staple 32 around anvil face 86 with anvil resting on top on driver 22.

Camming bar 42 is adapted to cam anvil face 86 upwards when driver 22 is deactivated and drawn rearwardly by reverse action of trigger element 20 upon completion of the crimping of staple 32 in crimping recess 30, specifically second pocket 58. Further rearward movement of driver 22 causes anvil face 86 to settle against the middle are of camming bar 42 so that anvil face 86 is positioned in an upward position as shown in FIG. 2 at the completion of the cycle. It is to noted that anvil face 86 moves upward when anvil face 86 is being decoupled from staple 32.

Inner end area 78 of anvil 74 is positioned immediately forward of driver camming ramp 64 in elongated hole 40B when stapler 10 and driver 22 are in the inactivated position illustrated in FIG. 2 while camming ramp 88 is generally raised from hole 40A. This is one extreme position of anvil 74 as it pivots about pivot pin 84.

It is to be particularly noted that outer lateral edges of second pocket 58 of driver 22 hold formed staple 32B in a horizontal path while anvil face 8 is withdrawn upwardly from its path thereby allowing unobstructed dispensing of staple 32.

Figures 12, 13:
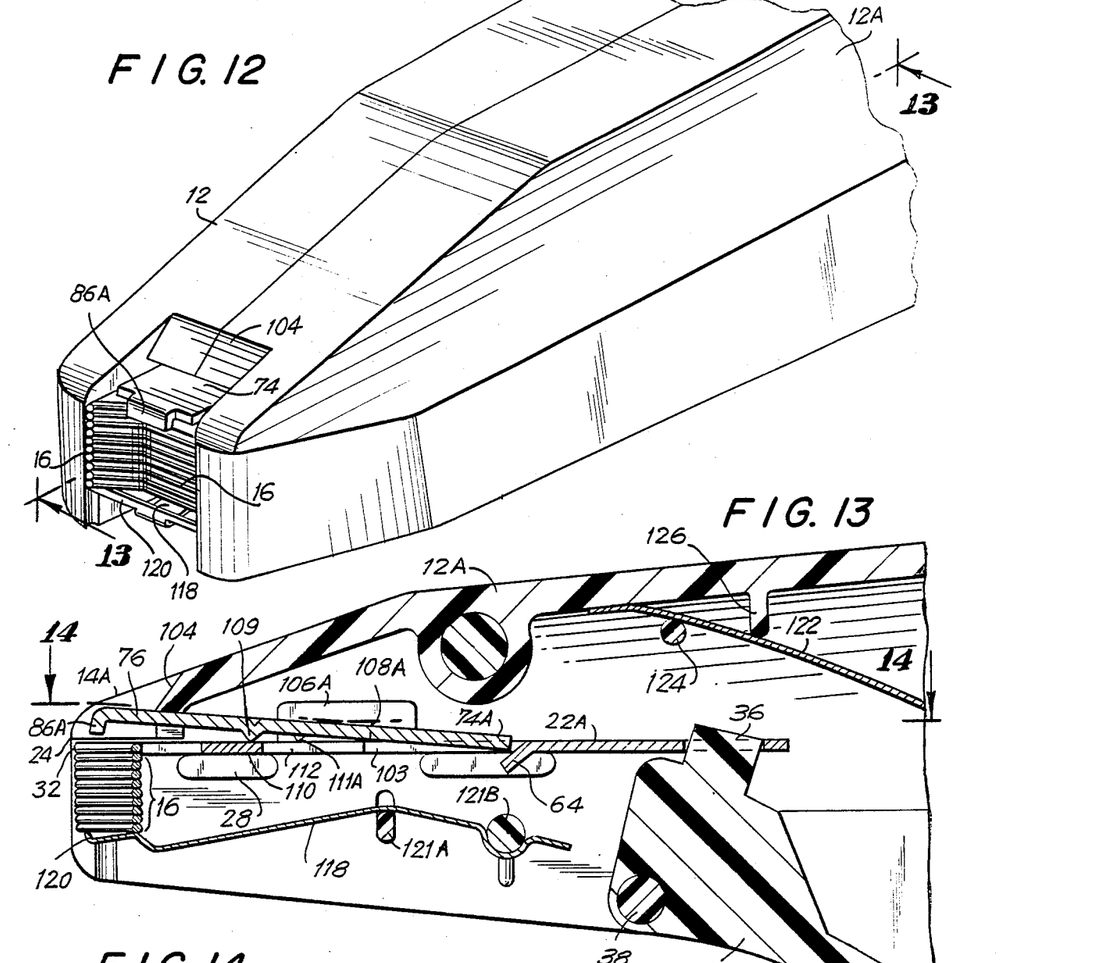
FIG. 12 is a perspective view of another embodiment of the nose and stack.
FIG. 13 is a partial side sectional view of another embodiment of the invention consistent with the embodiment shown in FIG. 12.
Figure 14:
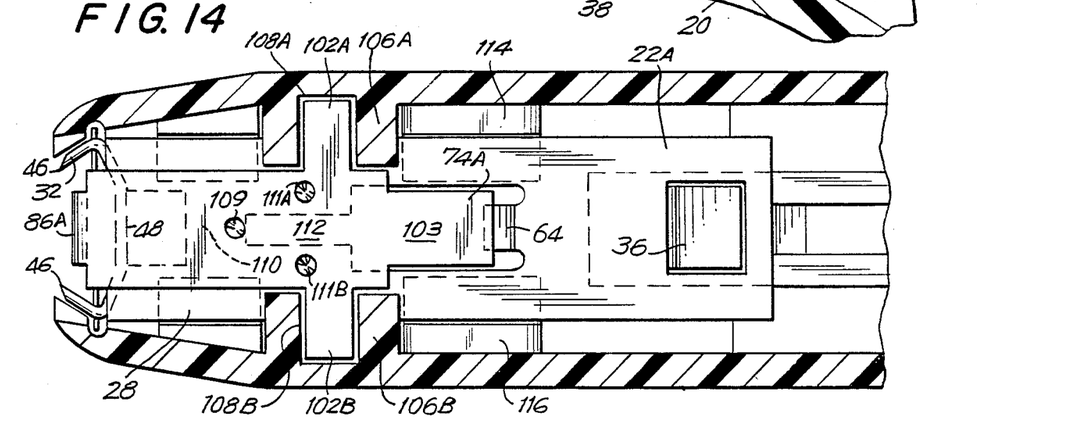
FIG. 14 is a view taken through line 14—14 of FIG. 13.
Figure 15:
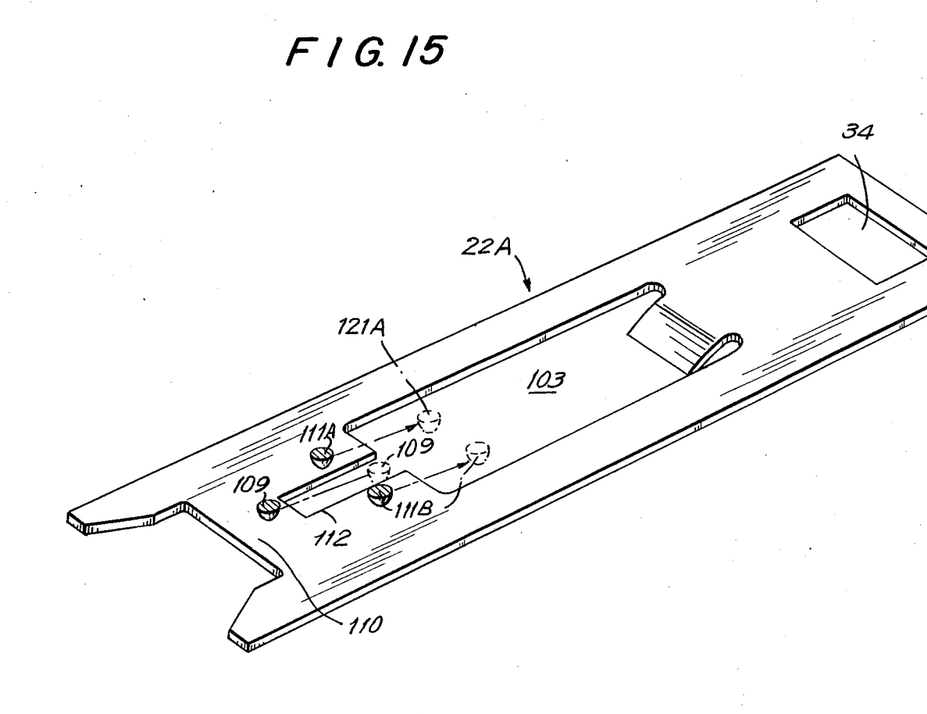
FIG. 15 is a perspective view of the anvil of the stapling mechanism shown in FIGS. 14 and 15.

When the crimping of staple 32 in second pocket 58 is completed, driver 22 is pulled back by a biasing element connected to frame 12 and the upper part of trigger element 20 in a manner to be explained later. The embodiment shown in FIGS. 12-14 illustrates a portion of the return biasing element, which as stated will be more fully described later in the description of these figures. It is to be particularly noted that in FIG. 6 driver 22 is withdrawn from contact with staple 32, which is now embedded in the tissue of the patient. Decoupling of closed staple 32, seen in FIGS. 6 and 9, is accomplished automatically, and closed staple 32 is left in the tissue as seen in FIG. 6.

When the surgeon repeats the action, trigger element 20 is pulled back, thus causing driver 22 to be activated and pushed forward by finger 36 so that camming ramp 64 of driver 22 pushes against the bottom of inner end area 78 of anvil 74 causing inner end area 78 to be forced upwardly about pivot pin 84 while simultaneously forcibly rotating front end 76 to move downward. Ramp 88 is subsequently displaced into hole 40A of driver 22 pending completion of the cycle wherein camming ramps 88 and 42 again come into contact to effect deactivation. Thus the outer end area 76, having been moved downward to a locked position, brings anvil face 86 to location immediately in front of mid-portion 48 of staple 32. As forward motion of driver 22 continues, staple 32 is restrained at mid-portion 48 by anvil face 86 of anvil 74. The continuation of the driver stroke advances pocket 54 forward and forces stationary staple 32 to conform to the following smaller pocket 58. This forming operation causes opposing arms 50 of staple 32 to rotate inwardly toward an imaginary lateral centerline until pointed ends 46 are proximate to one another. This crimping action when applied to a wound site brings the opposing edges of tissue 51 together and locks them into a secure closure. It is noted that staple 32 as a unit remains generally stable at the tissue throughout the activation operation except for the closure of ends 46 into tissue 51 during crimping. The completion of a stapling cycle ends when driver 22 has returned to its rearmost position. As driver 22 moves rearward, pocket 58 of driver 22 is withdrawn from side contact with formed staple 32. Concurrently the two camming ramps 88 and 64 of anvil 74 and driver 22 re-engage so as to cause front end 76 to rotate upward about pivot pin 84. Camming surfaces 78 of anvil 74 and driver 22 disposed at opposite ends of anvil 74 and driver 22 simultaneously disengage so as to allow rotation of anvil 74 to occur in a see-saw manner. Thus, anvil face 86, moving upward, is forcibly removed from engagement with midportion 48 of staple 32, thereby providing unobstructed dispensing of individual crimped staples 32B. Finally, a pivot motion from the engaged position to the non-engaged position is accomplished opposite to the pivot motion from the non-engaged to the engaged position previously described. One advantageous result of flanged anvil face 86 being engaged and disengaged in a see-saw manner is that nose 14 is very small and compact.

Anvil 74 includes a transverse holding flange 90 positioned at the edge of inner end area 78. Flange 90 extends upwardly towards the top of frame 12. A blocking element 92 unitary with frame 12 extends down from the top of frame 12 forward of and in contact with holding flange 90 as seen in FIGS. 2 and 3 so as to prevent any outward transitional movement of anvil 74, particularly during activation of driver 22. A holddown element 94 unitary with frame 1 extends down from the top of frame 12 directly over and in contact with shoulder 80 of anvil 74 as seen in FIGS. 2 and 3 so as to keep anvil 74 in its pivot motion about pivot pin 84 during its see-saw motion between engaged and non-engaged positions of anvil face 86. Driver 22 is positioned directly under and in contact with pivot pin 84 so that no upward motion of the driver is effected during activation, especially after camming ramp 88 leaves camming bar 42 and enters hole 40.

After staple 32 has been crimped and is demounted from stapler 10, another staple 32 is forced into first pocket 54 by upward pressure exerted upon the bottom of stack of staples 16 by a biasing plate spring 96 generally having a "U" configuration having upper and lower ends 96A and 96B, respectively and an inner portion 96C, which is the closed end of the U. Staple 32 is suitably retained in first pocket 54. Upper end 96A is configured to press upwardly against the bottom of the stack of staples so that after staple 32 in crimping recess 30 is crimped and driver 22 is withdrawn from the crimped staple spring 96 presses the next open staple into crimping recess 30 and first pocket 54 in particular.

Lower end 96B is wedged against a curved end of a bottom wall of frame 12 that is positioned slightly under and spaced inwardly from the bottom of stack of staples 16. Curved inner portion 96C is wedged against the top of a transverse spring holding upwardly extending portion of the bottom wall of frame 12. Spring 96 is in a biased mode during the entire upward movement of stack of staples 16 to the last staple used in the stack. Spring 96 can be slid out of the pocket it occupies for reloading stack of staples 16 and replaced.

An alternate to pivot pin 84 and shoulder 80 shown in FIGS. 2 and 3 is illustrated in FIGS. 4–9 and 12–15 wherein an anvil 74A similar to anvil 74 includes a pair of opposed pivot bars 102A and 102B extending transversely from the sides of anvil 74A transverse to an elongated hole 103 formed in a driver 22A (shown in detail in FIG. 15) similar to driver 22 and in contact with the upper surface of driver 22A. As seen in FIG. 13, a frame 104 at nose 14A that is in contact with the upper surface of outer end area of anvil 74A when anvil 74A is in its non-engaged mode and driver 22A is deactivated as shown in FIGS. 13 and 14. Frame 12A includes a pair of opposed bosses 106A and 106B that form a pair of opposed pivot bar recesses 108A and 108B, respectively, that are adapted to rotatably hold pivot bars 102A and 102B, respectively. FIGS. 13 and 14 illustrate a main, center, cone-shaped camming pin 109 extending downwardly from anvil 74A with a transverse camming bar 110 of driver 22A. Camming pin 109 is adapted to both keep anvil 74 raised in its non-engaging mode as seen in FIGS. 13 and 14 and to slidably meet camming bar 110 so as to be pressed upwardly from its engaged mode (not shown) in hole 103 when driver 24A is deactivated. A pair of slightly less protruding cone-shaped side pivot pins 111A and 111B that extend downwardly from anvil 74A are located rearwardly, or inwardly, and to the sides of camming pin 109. Hole 103 includes a narrow forward, or outward, channel 112 that acts to accept camming pin 109 when driver 22A is moved to the activated position, during which time pivot pins 111A and 111B slide on the top surface of driver 22A. When driver 22A becomes deactivated, camming pin 109 is moved out of its position in channel 112 so as to raise anvil 74A back to its deactivated position shown in FIGS. 13 and 14. FIG. 14 illustrates opposed elongated side positioning elements 114, 116 that are adapted to keep driver 22A in line during its forward and rearward movements.

FIGS. 12–14 also illustrate an alternate embodiment for activating stack of staples 16. A plate spring 118 for lifting stack of staples 16 includes a transverse bar holder 120 extending from the tip of plate spring 118 under stack of staples 16 extends under corners formed by the intersections side portions 50 and cross-portions 52. The inner portion of plate spring 118 is positioned over and under a pair of spaced transverse spring holders 121A and 121B, respectively. Anvil 74A includes a downwardly flanged anvil face 86A analogous to anvil face 86 of anvil 74 described earlier with regard to FIGS. 1–11.

FIGS. 2 and 3 and FIG. 13 illustrate a return biasing member, namely, a return plate spring 122 that is gripped to the upper inner area of frames 12 (FIGS. 2 and 3) and 12A (FIG. 13) by a pair of spaced spring holders 124 and 126 that extend transversely between the walls of frames 12 and 12A. In particular, the outer portion of spring plate 122 passes over transverse spring holder 124, which is preferably configured as a transverse cylinder, and further passes under spring holder 126, which extends downwardly from the top wall 128 of frames 12 and 12A. The inner portion of plate spring 122, that is the portion nearest the user, biases downwardly against the top surface 129 of trigger 20 where plate spring 122 is in sliding contact and applies downward pressure against the trigger. Plate spring 122 is generally unbiased in the inactivated mode of stapler 10 and driver 22 or 22A as shown in FIGS. 2 and 13, although there is a residual biasing action maintained in the inactive position to keep the trigger taut, and is generally fully biased when driver 22 or 22A is activated so that trigger 20 is biased back to the inactivated mode of stapler 10 so as to pull driver 22 or 22A back to its inactivated mode.

Figure 10:
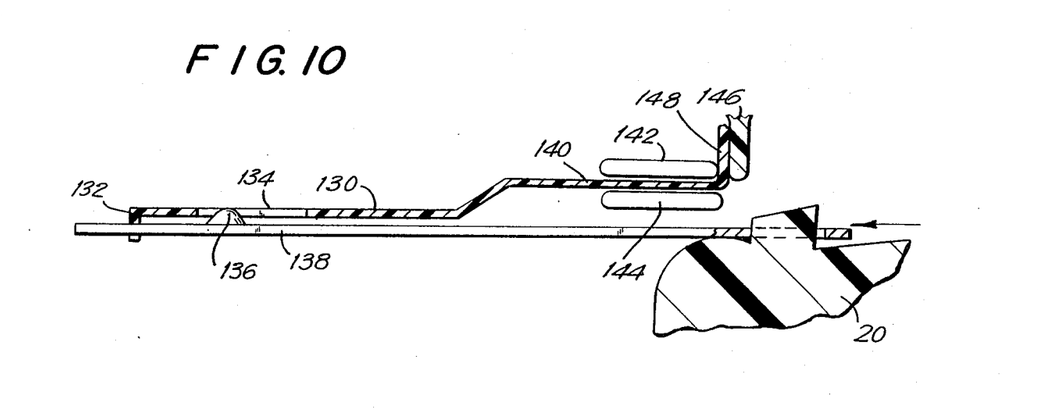
FIG. 10 is a side sectional view of a surgical stapler mechanism with the biasing element in the activated position.
Figure 11:
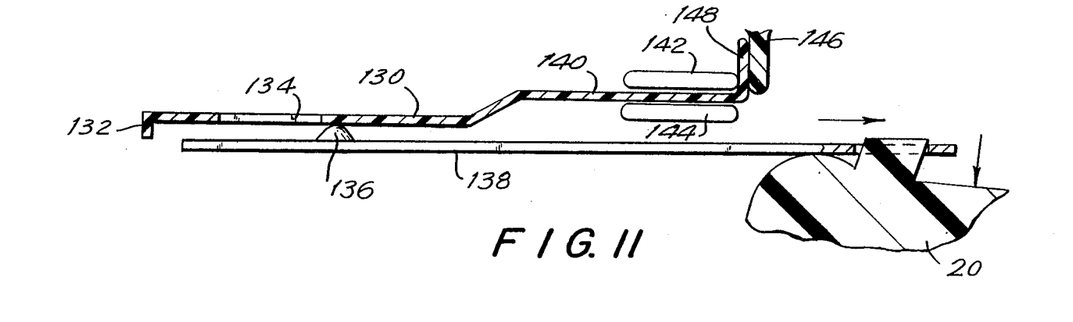
FIG. 11 is a side sectional view of a surgical stapler mechanism with the biasing element in the inactivated position.

Another embodiment of the invention is illustrated in FIGS. 10 and 11 where an anvil 130 is shown in its activated staple-crimping mode in FIG. 10 and in its non-activated staple-released mode in FIG. 11. Anvil 130 includes an outer end where a flanged anvil face 132 similar to anvil face 86 is schematically shown in its lowered activated position. Anvil 130 has a hole 134. A cone-shaped camming pin 136 extends upwardly from the upper side of a driver 138. In FIG. 10 driver 138 has been driven forward to its activated position by activation of a trigger the same as trigger 20 shown in FIG. 3 so that pin 136 extends through hole 134 so as to allow anvil face 132 to be biased downwardly by a spring biasing portion 140 located at the inner end of anvil 130, which is wedged by upper and lower gripping elements 142 and 144 which in turn are connected to a frame (not shown). The inner end of anvil 130 has an upwardly extending blocking flange 148 that is set against gripping elements 142 and 144 so as to prevent forward, or outward, movement of anvil 130. Rearward, or inward, movement of anvil 130 is prevented by a rearward blocking element 146 attached to the frame. FIG. 11 shows driver 138 pulled back with camming pin 136 removed from hole 134 and pressing upwardly against the undersurface of anvil 130 so that anvil face 132 of anvil 130 is in its raised, non-activated, staple-release position. Spring biasing portion 140 is generally unbiased in the activated mode of FIG. 10. Anvil 130 in effect pivots its inner, or rearward, end portion about gripping elements 142 and 144. When the crimping of staple 32 in second pocket 58 is completed, driver 138 is pulled back by a trigger the same as trigger 20 shown in FIGS. 2 and 3 by a biasing spring the same as plate spring 122 shown in FIG. 2.

An anti-double-staple loading safety feature of the invention shown in FIGS. 16–19 prevents trigger 20 from returning to its initial starting position until the full staple-crimping stroke has taken place, thereby preventing the next staple from entering crimping recess 30 and first staple pocket 54 in particular.

Figures 16, 17, 18, 19:
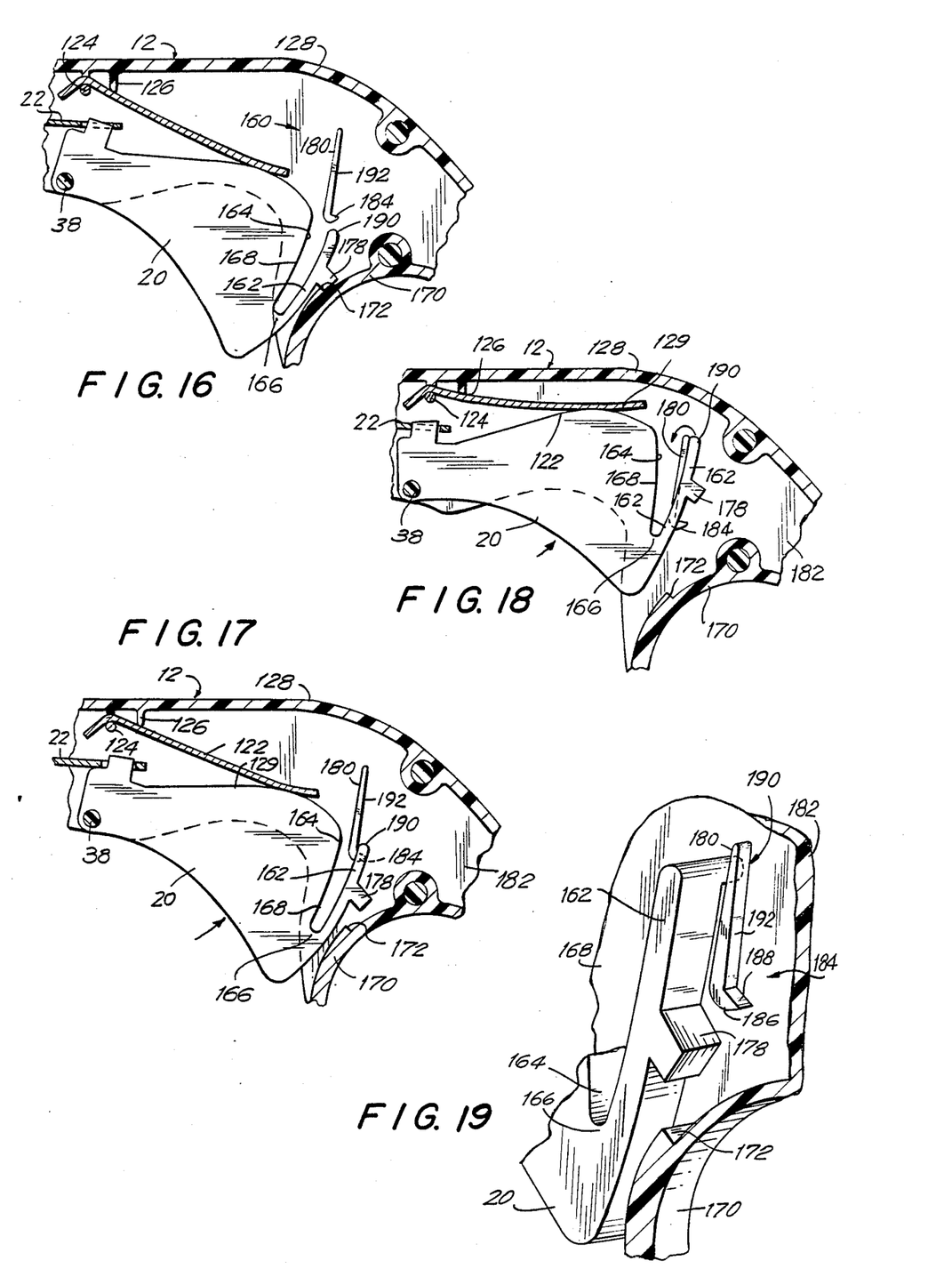
FIG. 16 is fragmented sectional view of a safety device shown in an inactive position.
FIG. 17 is a fragmented sectional view of the safety device shown in FIG. 16 in a partially activated position.
FIG. 18 is a fragmented sectional view of the safety device shown in a partially activated position following FIG. 17.
FIG. 19 is a fragmented perspective view of the safety device in FIGS. 16–17 in a position following that shown in FIG. 18.

To prevent such an occurrence, a safety device 160 shown in FIGS. 16–19 is positioned in frame 12 rearward of trigger 20. Device 160 includes a biasable safety finger 162 that is biasedly connected to the bottom portion of the rear wall 164 of trigger 20 at a connecting portion 166 and extends upwardly generally towards top wall 128 of frame 12. Safety finger 162 and rear wall 164 form an elongated slot 168 that is slightly arcuate in a forward direction and that is open at the top. A forwardly curved portion 170 of hand grip 18 (FIG. 1) forms a transverse stop wall 172 that faces generally upwardly and is adapted to stop the downward, or return, movement of trigger 20 as activated by return biasing spring 122 (as also shown in FIGS. 1 and 2) positioned between top wall 128 and the top side 129 of trigger 20 at a stop tab 178 that extends rearwardly from stop finger 162. An elongated camming member 180 is secured to a side wall 182 of frame 12 that is connected to upper wall 128. Camming member 180 is generally lateral in alignment with safety finger 162 and includes a camming lock portion 184 that extends rearwardly from the bottom end of camming member 180, that is, the end of camming member 180 nearest to the top of finger 162. Camming lock portion 184 has a curved bottom surface 186 and an opposed, upwardly facing flat locking wall 188, both of which are seen in FIG. 19. A cylindrical keeper pin 190 extends axially transverse from the top of finger 162 to a position proximate to side wall 182. Keeper pin 190 is shown in dotted line in FIGS. 16, 17, and 18, and is seen best in perspective view in FIG. 19. Keeper pin 190 is aligned in the same plane as camming member 180, and safety member 162 is generally extending laterally to camming member 180.

In operation, the surgeon pulls trigger 20 from the initial position shown in FIG. 16 where keeper pin 190 is spaced below camming ramp 184 to the position shown in FIG. 17 where keeper pin 190 has been forced outwardly relative to rear wall 164 of trigger 20 by the camming action of camming lock portion 184 so that keeper pin 190 is positioned at locking wall 188 and adjacent to rearward wall 192 of camming member 180. The result is that biasable camming member 162 is biased slightly rearwardly, that is, slot 168 is slightly larger than shown in FIG. 16. At this point, the safety feature of safety device 160 is operative. In particular, if the surgeon changes his mind or in general releases his hold on trigger 20, return bias spring 122 creates a bias against trigger 20 downwardly back toward the starting position along with driver 22. Camming lock portion 184, however, prevents this action from occurring, with the result that the surgeon, when he does continue, must move trigger 20 from the locked position it is in relative to camming member 180. Driver 22, likewise, is prevented from being pulled back with a partly crimped staple and possible with another staple being pressed upwardly from stack of staples 16 to create a double staple condition.

The surgeon then pulls trigger 20 farther back as shown in FIG. 17 so that keeper pin 190 is biasedly pressed against and drawn upwardly along rear wall 192 of camming member 180 with the result that camming member 180 is biased more than previously. During this time camming member 180 is positioned in the widening slot 168 as shown in FIGS. 17 and 18. Keeper pin 190 has almost reached the top of camming member 180. The safety feature of safety device 160 is still operative as long as keeper pin 190 is positioned along rear wall 192 since release of trigger 20 would result in return biasing spring 122 pressing keeper pin 190 back down to lock portion 184 to the position shown in FIG. 17.

The final movement that occurs with further drawing back of trigger 20 is indicated by an arrow in FIG. 18 with keeper pin 190 being passed to the tip of camming member 180 and finally over the top of camming member 180 as shown in FIG. 19 with keeper pin 190 being passed to and over the top of camming member 180 with the result that biasable safety finger 162 is self-biased back to its original unbiased mode, or shape, and its original spacing from rear wall 164. With keeper pin 190 free of any obstruction, return biasing spring 122 returns trigger 20 back to its original position shown in FIG. 16 along with safety finger 162. Keeper pin 190 is adapted to pass over the top of camming member 180 after staple 32 has been crimped in crimping recess 30 of driver 22.

Another embodiment of an anvil and driver mechanism for the stapler system is shown in perspective view in FIG. 20. An elongated, flat driver 22B similar to driver 22 shown and discussed relative to FIGS. 4–9 includes a crimping recess 30B the same as crimping recess 30; outer and inner end portions 24B and 26B; first and second holes 40C and 40D the same as first and second holes 40A and 40B, respectively; and a transverse support bar 68B between holes 40C and 40D. An anvil 74B generally analogous to anvil 74, except for a feature to be set forth, rests on top of driver 22B and is held in a stapler frame in the same manner as anvil 22 is held in frame 12. A pair of opposed pivot bars 102C and 102D the same as pivot bars 102A and 102B of anvil 74 extend transversely outwardly from the body of anvil 74B. A rear camming ramp 64B and a forward camming ramp 88B the same as camming ramps 64 and 88 of anvil 74 are adapted to ramp up the leading edge of forward hole 40C when driver 22B is activated forward by the trigger (not shown) to engage the staple. A driver finger (not shown) the same as driver finger 36 of the trigger is positioned in rear slot 34B of the anvil. Anvil 74B includes a downwardly flanged anvil face 86C the same as anvil face 86 described previously relative to anvil 74. Anvil 74B includes a forward portion 192 that extends between pivot bars 102C, 102D and anvil face 86C. Forward portion 192 tilts, or is angled, slightly upwardly from pivot bars 102C, 102D so that anvil face 86C is spaced slightly above driver 22B when the driver-anvil mechanism is in the non-engaged position shown in FIG. 20. When driver 22B is activated and driven forward, camming ramps 64B and 88B of anvil 74B are ramped at the adjacent camming bars of driver 22B to see-saw anvil 74B so that anvil face 86C is forced downwardly to engage the staple in recess 30B. Release of the trigger causes driver 22B to reverse and camming ramps 64B and 88B to ramp at the camming bars of the driver to reverse the see-saw motion of anvil 74B so that anvil face 86C is raised up so as to disengage from the crimped staple. The tilt, or angle, of forward portion 192 is preferably about 5°. The axis of rotation 194 of forward portion 192 is located along the front edge of pivot bars 102C and 102D.

Although the present invention has been described in some detail by way of illustration and example for purposes of clarity and understanding, it will, of course, be understood that various changes and modifications may be made in the form, details, and arrangements of the parts without departing from the scope of the invention as set forth in the following claims.

What is claimed is:

1. A surgical stapler for suturing tissue by at least one staple, comprising:
   frame means adapted to be held by a hand and having a nose, said frame means being for holding the staple and for directing the staple at the tissue site, said frame means having a hand grip,
   pivot means connected to said frame means,
   anvil means mounted in said frame means near said nose pivotably movable about said pivot means between non-engaged and engaged positions, driver means movably mounted in said frame means in operative association with said anvil means, said driver means having a crimping recess proximate said nose, the staple being capable of being shaped from an open staple to a crimped staple, said driver means being for forming said crimped staple in association with said anvil means in said crimping recess, said driver means being movable between activated and deactivated positions, wherein in said activated position said driver means has forced said anvil means from said non-engaged position to said engaged position, and wherein in said deactivated position said driver means has forced said anvil means from said engaged position to said non-engaged position, trigger means movable mounted to said frame means for activating said driver means for movement from said deactivated position to said activated position and simultaneously activating said anvil means for pivotable movement about said pivot means between said non-engaged position and said engaged position, said trigger means being adapted to manual activation, first camming means associated with said anvil means and said driver means for camming said anvil means into operative relationship with said driver means about said pivot means so that said anvil means is moved from said non-engaged position to said engaged position upon activation of said driver means for movement from said deactivated position to said activated position, and second camming means associated with said anvil means and said driver means for camming said anvil means about said pivot means so that said anvil means is moved from said non-engaged position to said engaged position upon activation of said driver means for movement from said deactivated position to said activated position.

2. The surgical stapler according to claim 1, further including return means connected to said frame means and to said trigger means for moving said driver means to said deactivated position.

3. The surgical stapler according to claim 2, wherein said trigger means is further being for activating said driver means for movement from said activated position to said deactivated position and simultaneously activating said anvil means for pivotable movement about said pivot means from said engaged position to said engaged position.

4. The surgical stapler according to claim 1, wherein said anvil means has an anvil face portion at said nose, said anvil face portion being movable between non-engaged and engaged positions.

5. The surgical stapler according to claim 4, wherein said driver means and said crimping recess are in a plane and said driver means is slidably movable relative to said anvil means so as to force said anvil means between said non-engaged and said engaged positions, wherein in said non-engaged position said anvil face portion is spaced from said plane and said crimping recess; and wherein in said engaged position said anvil face portion is in said plane adjacent to said crimping recess where said open staple is crimped between said crimping recess and said anvil face portion.

6. The surgical stapler according to claim 5, wherein said anvil means is a generally flat first elongated member and opposed inner and outer end areas, said anvil face portion being located at said outer end area, said first elongated member including said first camming means being located between said anvil face portion and said pivot means.

7. The surgical stapler according to claim 6, wherein said drive means is a second elongated member having opposed inner and outer end portions positioned in association with said inner and outer end areas, said crimping recess being formed at said outer end portion, said inner end portion being in operative relationship with said trigger means, said second elongated member forming an elongated hole spaced from said crimping recess, said hole including a main hole and a narrow channel extending outwardly from said main hole, said hole having a pair or transverse forward side edges on opposed sides of said channel, and said channel having a transverse lead edge, said second elongated member having a surface including camming areas forwardly of said lead edge and said side edges, said first camming means of said first elongated member being in contact with said surface when said anvil face portion is in said non-engaged position, and said first camming means being positioned in said hole when said anvil face portion is in said engaged position.

8. The surgical stapler according to claim 6, wherein said driver means is a generally flat second elongated member having opposed inner and outer end portions associated with said inner and outer end areas, respectively, of said first elongated member, said crimping recess being formed at said outer end portion, said inner end portion being in operative relationship with said trigger means, said second elongated member forming an elongated hole spaced inwardly from said crimping recess, said hole and said crimping recess being separated by a transverse camming bar, said camming bar being in contact with said first camming means of said first elongated member when said anvil face portion is in said non-engaged position, and said camming bar being spaced from said first camming means when said anvil face portion is in said engaged position.

9. The surgical stapler according to claim 8, wherein said first camming means is a transverse first ramp angled rearwardly from said first elongated member toward said second elongated member, said first ramp being in contact with said camming bar of said second elongated member in said non-engaged position of said anvil face portion and being spaced from said camming bar in said engaged position, said camming bar being adapted to cam said first elongated member at said first ramp during rearward movement of said driver means from said activated position to said deactivated position wherein said anvil face portion is moved to said non-engaged position.

10. The surgical stapler according to claim 9, wherein said open staple includes a transverse mid-portion, a pair of outwardly angled side portions connected to opposite sides of said mid-portion, a pair of inwardly angled crossportions connected to said side portions, and a pair of spaced pointed ends at said side portions, said crimping recess including an outward positioning pocket and an inward crimping pocket adjacent to said positioning pocket, said positioning recess being defined by opposed angled edges adapted to lie in contact with said pair of angled crossportions, said open staple being positioned in said positioning pocket when said anvil face portion is in said non-engaged position and said second elongated member is in said deactivated position.

11. The surgical stapler according to claim 10, wherein said crimped staple includes said side portions being generally opposed and parallel and generally perpendicular to said mid-portion, said cross-portions being generally in line and generally parallel with said mid-portion, and said pointed ends being proximate, and wherein said crimping pocket is defined by a transverse edge of said second elongated member and a pair of opposed generally parallel side edges, said crimping pocket recess having an open side opposite said transverse edge adjacent said positioning pocket recess, said transverse edge being adapted to be in contact with said transverse mid-portion of said closed staple and said pair of opposed generally parallel side edges being adapted to be in contact with said side portions of said crimped staple.

12. The surgical stapler according to claim 11 further including safety means connected to said trigger means and to said frame means for preventing said return means from returning said driver means to said deactivated position until said open staple has been crimped to said crimped staple, wherein another staple is prevented from entering said positioning pocket before completion of the staple-crimping stroke of said second elongated member.

13. The surgical stapler according to claim 12, wherein said safety means includes a biasable finger member secured to the rearward portion of said trigger means and a camming member including a rear wall and a lock portion at said rear wall, and said finger member having a keeper pin at the tip of said finger member, said keeper pin being adapted to be biasedly pressed against the rear wall of said camming member upon activation of said trigger means and said keeper pin having been resiliently pressed past said lock portion, said anvil face portion having been moved to said engaged position upon said keeper pin having passed said lock portion, said return means being activated to draw said keeper pin no further than said lock portion upon release of said trigger means while said keeper pin is in pressing contact with said rear wall of said trigger means.

14. The surgical stapler according to claim 13, wherein said camming member has a top end, said trigger means being adapted to pass said keeper pin past said top end, said keeper pin being biased back to said rear portion of said trigger means upon passing said top end, said second elongated member having crimped said staple, whereupon said return means is capable of returning said trigger means to a position wherein said second elongated member is returned to said inactivated position.

15. The surgical stapler according to claim 11, wherein said anvil face portion includes a transverse anvil flange extending into said crimping recess and pressed against said transverse mid-portion of the staple in turn positioned in pressing contact at said transverse edge of said second elongated member when said anvil flange is in said engaged position; said anvil flange being spaced from said plane of said crimping recess when said anvil flange is in said non-engaged position.

16. The surgical stapler according to claim 15, wherein said inner end area is positioned in said hole of said second elongated member in said non-engaged position of said anvil flange, said inner end portion of said second elongated member having a surface disposed between said first and second elongated members, said inner end area being in contact with said surface inward of said hole in said hole in said engaged position of said anvil flange.

17. The surgical stapler according to claim 16, wherein said second elongated member has a slot at said inner end portion spaced inwardly from said hole, and wherein said trigger means includes a trigger member having an internal finger and a transverse pivot connected to said frame means, said trigger member being rotatably mounted to said frame means at said transverse pivot, said finger being movably positioned in said slot, whereby rearward operation of said trigger member results in forward movement of said second elongated member to said activated position.

18. The surgical stapler according to claim 16, wherein said second elongated member forms second camming means is located at said inner end portion for camming said inner end area of said first elongated member from said hole about said pivot means to said surface of said second elongated member at said outer end portion as said second elongated member is moved from said deactivated position to said activated position upon manual activation of said trigger means.

19. The surgical stapler according to claim 18, wherein said second camming means is a second transverse ramp connected to said driver, said ramp extending forwardly and away from both said plane of said second elongated member and said first elongated member, said second transverse ramp being adapted to contact and raise said inner end area of said first elongated member so as to cause said first elongated member to rotate about said pivot means and to cause said anvil flange to be rotated from said non-engaged position to said engaged position.

20. The surgical stapler according to claim 19, wherein said pivot means is a pair of opposed pivot bars extending transversely from said first elongated member transverse to said elongated hole in contact with said surface of said second elongated member, said frame means including a hold-down element at said nose in contact with said outer end area of said first elongated member, said frame means forming a pair of opposed pivot bar recesses adapted to rotatably hold said pivot bars.

21. The surgical stapler according to claim 20, wherein said generally flat first elongated member includes a generally flat forward portion extending between said pivot means and said outer end area and a generally flat rearward portion extending between said pivot means and said inner end area, said forward portion being located at a slight distance from said anvil face portion of said second elongated member.

22. The surgical stapler according to claim 21, wherein said forward portion forms a slight angle with said rearward portion.

23. The surgical stapler according to claim 22, wherein said slight angle is approximately 5°.

24. The surgical stapler according to claim 19, wherein said pivot means is a transverse cylindrical pivot pin connected to said frame member; and wherein said first elongated member includes a transverse shoulder forming a transverse generally semi-cylindrical pivot recess in which said pivot pin is seated, said frame means including a transverse hold-down element in contact with said shoulder, said first elongated member being pivotably movable about said pivot pin between said engaged and non-engaged positions.

25. The surgical stapler according to claim 15 wherein said inner end area of said first elongated member includes locking means for preventing outward transitional movement of said first elongated member during movement of said second elongated member from said inactivated position said activated position.

26. The surgical stapler according to claim 25, wherein said locking means includes said first elongated member having a locking flange and said frame means including a stop member located inwardly of said locking flange, said locking flange being slidably engaged with said stop member; wherein when said first elongated member rotates about said pivot means, said locking flange remains slidably engaged with said stop member.

27. The surgical stapler according to claim 15, wherein said second elongated member includes a transverse bar located at said pivot means, said elongated hole including inward and outward portions defined on opposite sides of said transverse bar, said inner and outer end areas of said first elongated member being adapted to being positioned in said inward and said outward end areas, respectively, in said non-engaged and said engaged positions, respectively.

28. The surgical stapler according to claim 4, wherein said return means is a spring connected to said frame means and to said trigger means, said return means being biased when said drive means is in said activated position and unbiased when said drive means is in said deactivated position.

29. The surgical stapler according to claim 1, wherein said first camming means includes a main cone-shaped camming pin adapted to pass over said transverse lead edge and a pair of cone-shaped side pins adapted to pass over said forward side edges, said pair of side pins being slightly less protruding than said main pin, said side pins being spaced from said side edges and said main pin being adjacent to said lead edge when said anvil face portion is in said non-engaged position, and said side pins being positioned in said main hole and said main pin being positioned in said channel when said anvil face portion is in said engaged position, whereby said first elongated member is gradually cammed when being moved between said engaged and non-engaged positions.

30. The surgical stapler according to claim 1, wherein said at least one staple includes a plurality of staples positioned in said frame means adjacent said crimping recess, said at least one staple being positioned in said crimping recess.

31. The surgical stapler according to claim 20, wherein said plurality of staples is in the configuration of a stack of staples having one end at said crimping recess and an opposed end generally transverse to said crimping recess.

32. The surgical stapler according to claim 30, further including a cartridge, said plurality of staples being held in said cartridge, said cartridge having one end at said crimping recess and an opposed end generally transverse to said crimping recess.

33. The surgical stapler according to claims 21 and 32, further including stapler spring means for pressing against said opposed end so that after said second elongated member is withdrawn from said crimped staple, the next staple is pressed into said positioning pocket.

34. The surgical stapler according to claim 33, wherein said spring means is a U-shaped biasing spring positioned in said frame means, said U-shaped spring having opposed ends, one of said ends being in operative contact with said opposed end of said plurality of springs, and the other of said ends being in resistant contact with said frame means.

35. The surgical stapler according to claim 34, wherein said spring means is a flat spring positioned is said frame means, said flat spring having opposed ends, one of said ends being in operative contact with said opposed end of said plurality of springs and the other of said ends being in resistant contact with said frame means.

36. The surgical stapler according to claim 30, wherein said plurality of staples is approximately 15 staples.

* * * * *